(12) United States Patent
Selzer et al.

(10) Patent No.: US 6,986,906 B2
(45) Date of Patent: Jan. 17, 2006

(54) CRANBERRY BASED DIETARY SUPPLEMENT AND DENTAL HYGIENE PRODUCT

(75) Inventors: Jonathan Selzer, New Haven, CT (US); Franklin M. St. John, Wallingford, CT (US)

(73) Assignee: Herbasway Laboratories, LLC, Wallingford, CT (US)

( * ) Notice: Subject to any disclaimer, the term of this patent is extended or adjusted under 35 U.S.C. 154(b) by 437 days.

(21) Appl. No.: 10/425,583

(22) Filed: Apr. 29, 2003

(65) Prior Publication Data

US 2003/0203054 A1 Oct. 30, 2003

Related U.S. Application Data

(63) Continuation-in-part of application No. 09/962,771, filed on Sep. 25, 2001, now abandoned.

(51) Int. Cl.
*A01N 65/00* (2006.01)
*A61K 35/78* (2006.01)

(52) U.S. Cl. .................. 424/732; 424/725; 424/757; 424/773; 424/774; 424/777

(58) Field of Classification Search ............... 424/732, 424/725, 757, 773, 774, 777
See application file for complete search history.

(56) References Cited

U.S. PATENT DOCUMENTS

| | | | |
|---|---|---|---|
| 5,411,755 A * | 5/1995 | Downton et al. | 426/599 |
| 5,433,965 A * | 7/1995 | Fischer et al. | 426/548 |
| 6,103,240 A | 8/2000 | Zhou | |
| 6,124,442 A | 9/2000 | Zhou et al. | |
| 6,238,707 B1 | 5/2001 | Chun | |
| 6,461,659 B1 * | 10/2002 | Zhou | 426/548 |
| 6,652,891 B2 * | 11/2003 | Selzer | 424/725 |
| 2004/0161478 A1 * | 8/2004 | Nakagiri et al. | 424/725 |

OTHER PUBLICATIONS

A-Type Proanthocyanidin Trimers from Cranberry that Inhibit Adherence of Uropathogenic P-Fimbriated *Escherichia coli*, Foo et al., J. Nat. Prod. 2000, 63, 1225-1228.
Effect of Cranberry Juice on Bacteriuria in Children with Neurogenic Bladder Receiving Intermittent Catheterization, Theresa A. Schlager, The Journal of Pediatrics, V 135(6), Dec. 1999, pp 698-702.
Prevention of Recurent Urinary-Tract Infections in Women (Commentary) Ann Stapleton, The Lancet, V 353(9146), Jan. 2, 1999, pp 7-8.
Reduction of Bacteriuria & Pyuria After Ingestion of Cranberry Juice, Avorn et al., JAMA, V 271(10), Mar. 9, 1974, 751-754.
Loss of Fimbrial Adhesion with the Addition of Vaccinum Macrocarpon to the Growth Medium of P-Fimbriated *Escherichia coli*, Ahuja et al., J Urol Feb.1998, 159(2): 559-62.

In Vitro Anticancer Activity of Fruit Abstracts from Vaccinium Species, Bomser et al, Planta Med., Jun. 1996, 62(3), 212-6.
First-Time Urinary Tract Infection & Sexual Behavior, Foxman et al, Epidemiology, Mar. 1995, 6(2), pp 162-8.
Urinary Problems After Formation of a Mitrofanoff Stoma, Prof Nurse, Jan. 1995, 10(4), pp 221-4.
Identification of Procyanidins & Anthocyanins in Blueberries & Cranberries (*Vaccinium* spp.) Using High-Performance Liquid Chromatography/Mass Spectrometry, Prior et al, J. Agric Food Chem, Mar. 2001, 49(3), pp 1270-6.
Cranberry Juice Consumption May Reduce Biofilms on Uroepithelial Cells: Pilot Study in Spinal Cord Injured Patients, Reid et al, Spinal Cord, Jan. 2001, 39(1), pp 26-30.
A High Molecular Mass Constituent of Cranberry Juice Inhibits Helicobactor Pylori Adhesion to Human Gastric Mucus, Burger et al, FEMS Immunol Med Microbiol, Dec. 2000, 29(4), pp 295-301.
A-Type Proanthocyanidin Trimers from Cranberry that Inhibit Adherence of Uropathogenic P-Fimbriated *Escherichia coli*, Foo et al, J. Nat Prod, Sep. 2000, 63(9), pp 1225-8.
The Structure of Cranberry Proanthocyanidins Which Inhibit Adherence of Uropathogenic P-Fimbriated *Escherichia coli* in vitro, Foo et al, Phytochemistry, May 2000, 54(2), pp 173-81.
Effects of Blueberry & Cranberry Juice Consumption on the Plasma Antioxidant Capacity of Healthy Female Volunteers, Pedersen et al, Eur J Clin Nutr, May 2000, May 2000, 54(5), pp 405-8.
Influence of Cranberry Juice on Attachment of *Escherichia coli* to Glass, Allison et al, J Basic Microbiol, 2000, 40(1), pp 3-6.
Effect of Cranberry Juice on Bacteriuria in Children with Neurogenic Bladder Receiving Intermittent Catheterization, Schlager et al, J Pediatr, Dec. 1999, 135(6), pp 698-702.
Inhibiting Interspecies Coaggregation of Plaque Bacteria with a Cranberry Juice Constituent, Weiss, et al, [published erratam appear in J Am Dent Assoc, Jan. 1999, 130(1), 36 and Mar. 1999, 130(3), p 332], J Am Dent Assoc, Dec. 1998, 129(12), pp 1719-1723.
Cranberry Extract Inhibits Low Density Lipoprotein Oxidation, Wilson et al, Life Sci, 1998, 62(24), PL381-PL386.
Antioxidant Capacity in Cranberry is influenced by Cultivar and Storage Temperature, Wang, J Agric Food Chem, Feb. 2001, 49(2), 969-74.

* cited by examiner

Primary Examiner—Herbert J. Lilling
(74) Attorney, Agent, or Firm—Carmody & Torrance LLP

(57) ABSTRACT

A cranberry based dietary supplement or dental hygiene product is revealed with enhanced flavor characteristics. Cranberry sources are combined with extracts of the fruit of Lou Han Kuo and/or extracts from the leaves of Stevia rebaudiana and/or extracts from the leaves of Chinese Blackberry. Extract from the root of Chinese licorice is used as a stabilizer in the composition. The resulting product is a pleasant tasting dietary supplement, which is easily absorbed by the body in liquid form, and provides substantially therapeutic effects.

9 Claims, No Drawings

CRANBERRY BASED DIETARY SUPPLEMENT AND DENTAL HYGIENE PRODUCT

This is a continuation-in-part of application Ser. No. 09/962,771, filed Sep. 25, 2001, now abandoned.

FIELD OF THE INVENTION

The present invention relates to cranberry based compositions with improved taste, and to a method for using such compositions as dietary supplements, therapeutic supplements and/or as dental hygiene products.

BACKGROUND OF THE INVENTION

The uses of cranberry as a therapeutic supplement are manifold and well documented in the scientific literature. Current research around the world is substantiating further claims for traditional herbal medicines.

The most well documented therapeutic effect of cranberry concerns urinary tract infections. For many years it has been recognized that cranberry juice helps to relieve and possible cure urinary tract infections such a bladder and urethra infections. Originally, this effect was considered to be a result of lowered urinary pH (increased acidity) after ingestion of cranberry. The lowered pH was thought to make the urine an inhospitable milieu for the growth of pathogenic bacteria, such as *E. Coli*. The bacteria would not grow and would be washed through the system and excreted from the body with the urine. It has recently been discovered, that certain components of cranberry, the proanthocyanidins, possess specific properties which inhibit the adhesion of pathogenic bacteria to the wall of the urinary tract. Without a hold, the bacteria are easily flushed with the urine and excreted. In some cases, cranberry has been at least as, if not more, effective in preventing urinary tract infections than the commonly prescribed antibiotics.

Furthermore, recent studies have shown that cranberry is a very potent antioxidant and can help to protect cells from free-radical damage. Free radical damage has been implicated in a great many diseases and conditions, from Parkinson's disease to coronary heart disease and cancer.

Recent studies have also demonstrated the inhibiting effects of cranberry on *Helicobacter pylori*, a pathogenic bacteria responsible for ulcers. Cranberry may have further use in the treatment and prevention of heart disease, breast cancer and periodontal disease.

Even before the appearance of scientific literature, many people have been consuming cranberry products as either therapeutic herbal supplements or refreshing drink or both. Most products presented as dietary supplements are in the form of capsules and tablets.

The cranberry extracts and powders utilized in these products are of varying qualities, ranging from spray-dried cranberry juice powder to dehydrated whole cranberry powder. By far, the latter contains more of the components in cranberry, which are considered responsible for its therapeutic effects. Most of the products on the market are manufactured with the cranberry juice spray dried onto maltodextrine or other carriers. This process requires prolonged exposure to elevated temperatures, which are suspected to degrade some of the therapeutically active ingredients of cranberry.

In the case of capsules, the spray-dried powder is packaged in either hard gelatin or chemically modified wood cellulose capsules. Many consumers object to the use of these substances as either (a) animal by products or (b) chemically derived. Capsules pose a problem for the elderly and young, who may experience difficulties in swallowing such objects. Furthermore, the delivery and absorption of the cranberry powder in the digestive system is affected by the use of capsules, which must dissolve to release their contents. On the other hand, drinks which contain sufficient cranberry content to achieve beneficial effects can be objectionable because of the intense acidity of the cranberry.

Thus, it is an object of this invention to reveal a cranberry based composition with sufficient cranberry concentration such that it provides substantial beneficial and therapeutic effects when consumed yet has a pleasant flavor. It is a further object to this invention to enhance the therapeutic benefits of cranberry by combining it with flavor enhancing additives which themselves have beneficial therapeutic properties but which do not have the problems associated with the use of sugar.

SUMMARY OF THE INVENTION

The inventors herein propose combining cranberry juice, cranberry juice powder or whole cranberry fruit powder with one or more additives selected from the group consisting of extracts derived from the fruits of Lou Han Kuo (i.e. Lou Han), extracts derived from the leaves of stevia, and/or, extracts derived from the leaves of Chinese Blackberry to produce an aqueous drink. The inventors have discovered that dietary supplements prepared in accordance with the foregoing produce a great tasting herbal product which possesses many beneficial therapeutic properties, including the ability to relieve urinary tract infections, antioxidant properties, antibiotic properties and the ability to soothe the digestive system.

Alternatively, the foregoing herbal combination can be formulated into a toothpaste or dental gel by combining the foregoing active ingredients with a thickener or gel or they can be formulated into an effective mouthwash. These oral hygiene products produce a delicious and effective natural alternative to typical synthetic toothpastes and mouthwashes currently available.

DETAILED DESCRIPTION OF THE INVENTION

The inventors herein propose a dietary supplement and/or oral hygiene products comprising:

(a) cranberry juice, cranberry juice powder and/or cranberry whole fruit powder; and (b) at least one additive selected form the group consisting of (i) extracts of the fruits of Lou Han, (ii) extracts from the leaves of Stevia, and (iii) extracts from the leaves of Chinese Blackberry.

Additional optional ingredients include xylitol, fructose or other preferably low glycemic sugars, vitamins, minerals, other herbal extracts, stabilizers such as Chinese Licorice root extracts, and thickeners or gelling agents. The combination of the foregoing ingredients provides a great tasting dietary supplement or dental hygiene product which possesses the therapeutic properties provided for herein.

The dietary supplement or oral hygiene product described herein requires a source of cranberry. The inventors have found cranberry juice, (including cranberry juice concentrate), cranberry juice powder, and/or whole cranberry fruit powder to be useful sources of cranberry for use in this invention. Cranberry juice powder and whole cranberry powder are preferred because of their concentrated form. Whole cranberry powder is most preferred because it presents the most natural concentrated form of cranberry with the lowest potential of losing beneficial cranberry constituents through its processing. In choosing a source of cranberry, it is preferred that the source of cranberry not be subjected to high temperatures in its manufacture, since excessive heating is believed to degrade certain beneficial constituents of cranberry. The concentration of cranberry in the dietary supplement or oral hygiene product, on a dry basis, may range from about 1% to 25% by weight. In the dietary supplement, the concentration of cranberry, on a dry basis, is preferably from about 5% to 15% by weight. In the oral hygiene product, the concentration of cranberry, on a dry basis, is preferably from about 1% to 5% by weight.

The dietary supplement or oral hygiene product described herein also requires at least one additive selected from the group consisting of (i) extracts of the fruits of Lou Han, (ii) extracts from the leaves of Stevia, and (iii) extracts from the leaves of Chinese Blackberry. Preferably more than one or all of the foregoing additives are present in the composition. The concentration of the foregoing additives in the composition may range in concentration depending upon the concentration of the extracts themselves. Generally, these extracts are provided as dried powders and if so, the concentration of these additives in the composition of this invention will range from about 0.05% to 6% by weight but is preferably from about 0.05% to 1% by weight.

Lou Han (Kuo) fruit comes from Momordica grosvenori also called Siraitia grosvenorii. Lou Han is native to the People's Republic of China and Japan and is an edible fruit having an intensely sweet taste. It is reputed to possess healing properties for lung congestion, colds, sore throats, digestive and urinary disturbances, as well as antibiotic and antiseptic properties. Extracts of both fresh and dried Lou Han are available throughout the world, and can be readily purchased. One suitable aqueous extract is available from the Shaanxi Youthsun Company located in China. Various methods are known for preparing extracts of the Lou Han fruit, and other natural sources, such as those methods described in the U.S. Pat. Nos. 6,124,442 and 4,084,010, the teachings each of which are incorporated herein by reference in their entirety.

The preferred extracts of Lou Han are prepared as noted above using water or water/alcohol mixtures to extract the active species from the plant, thereby creating an aqueous extract. One such preferred method is described in U.S. Pat. No. 6,124,442, wherein the starting plant source material is fresh plant material such as cut pieces of freshly harvested Lou Han Kuo fruit. These fresh plant pieces are extracted by soaking in a bath of heated (80° F.–212° F.) water, alcohol (preferably ethanol) or both. This initial process is preferably carried out in hot, preferably boiling water or water/alcohol mixture. Extraction in the bath may be carried out several times, each time saving the resulting liquid. The resulting extract liquid is then filtered through a suitable filter, such as a 40-mesh stainless steel screen. The thus-obtained solid material can then be extracted again. It may be preferable for a particular process to carry out more or less extraction steps with different volumes of liquid being used for each boiling or extraction step. The result of this extraction process is an aqueous, alcohol or aqueous/alcohol extract that can be used in the composition of this invention. The extract can be used directly or concentrated by evaporation or spray drying and then used. Other extracts herein such as extract of the leaves of stevia, extracts of the leaves of Chinese Blackberry or extracts of the root of Chinese licorice are made in the same way. If alcohol is used, alone or with water, it is preferably ethanol.

Stevia rebaudiana (Stevia) is also a plant which is native to the People's Republic of China. Extracts from the leaves of Stevia are commonly known and have been used as a natural sweetener in Asia for many years. Studies have demonstrated that extracts from the leaves of Stevia can have a variety of beneficial therapeutic effects including antibiotic properties especially against E.Coli, vasodilatation properties especially in the kidney, anti-hypertensive effects, beneficial effects on pancreatic beta cells, and enhancing the secretion of insulin. Extracts from the leaves of Stevia are known and can be purchased for use in formulating the compositions described herein. These extracts can be prepared using the same or similar techniques used for preparing extracts for Lou Han as noted above. One suitable aqueous extract is available from the Shaanxi Youthsun Company located in China.

Extracts from the leaves of Chinese Blackberry (Rubus Suavissimus) are also known and can be purchased for use in formulating the compositions described herein. One suitable aqueous extract is available from the Shaanxi Youthsun Company located in China. The active ingredients in these extracts are believed to comprise diterpene glycosides. Extracts of the leaves of Chinese Blackberry have been used as natural sweeteners. A variety of therapeutic benefits have been ascribed to extracts of the leaves of Chinese Blackberry including relief from pre-menstrual syndrome, beneficial effects upon the kidney, and other beneficial effects. Extracts of the leaves of Chinese Blackberry can be prepared using the same or similar techniques used for preparing extracts of Lou Han as noted above.

As noted, other optional materials may be included in the composition of this invention. Vitamins, minerals or other herbal extracts may be added for particular purposes or effects. Sugars such as fructose may be added but are not recommended. Artificial sweeteners such as xylitol may be added and may be beneficial in formulating toothpaste or dental gels from the compositions of this invention. Preferably the composition is substantially free of sucrose. Further, when formulating toothpastes or dental gels with the composition of this invention, thickeners or gelling agents should be employed. Other flavoring agents such as natural cranberry flavor may also be utilized. Glycerin has also proven to be a beneficial additive.

Stabilizers for the compositions of this invention may also be employed to preserve the flavor and other properties of the product. The inventors have found that extracts from the root of the Chinese licorice (Glycyrrhiza uralensis) have proven to be excellent stabilizers for the products described herein as well as flavor enhancers. Extracts of the root of Chinese licorice are known and can be purchased for use in this invention. Suitable extracts include extracts available from the Shaanxi Youthsun Company located in China and aqueous extracts available from the Fortune Bridge Co., Inc. of Elmont, N.Y. These extracts have been used for their beneficial medicinal properties for years. If used, the concentration of Chinese licorice extract in the composition of this invention may preferably range from 0.001% to 1.0% by weight. The Chinese licorice root extract is preferably made using the same methods as noted above for the extracts of Lou Han Kuo fruit.

In preparing the compositions of this invention for use as dietary supplements, the ingredients noted herein are merely combined with water in the concentrations noted to form a dietary supplement drink. It is recommended that the consumer of the product ingest three or more four-ounce servings of the product per day, such that approximately 500 mg of cranberry on a dry basis, are ingested per day. In preparing the compositions described herein as toothpaste or a dental gel, the ingredients taught herein are combined with small quantities of water and appropriate thickeners or gelling agents,.

The compositions of this invention are further described in the following examples which should be taken as illustrative only and not limiting in any manner.

EXAMPLE I

A cranberry based dietary supplement was prepared using the following ingredients:

| Component | % by Weight |
| --- | --- |
| Whole cranberry power[1] | 1.0 |
| Lou Han extract powder[2] | 2.5 |
| Chinese licorice extract[3] | 0.1 |
| Natural cranberry flavor[4] | 2.5 |
| Glycerin | 33.0 |
| Water | 51.9 |

[1]Available from the Artemis Company
[2]Available from Shaanxi Company
[3]Available from Shaanxi Company
[4]Available from the Virginia Dare Company The foregoing ingredients were blended to form a pleasant tasting dietary supplement which is believed to exhibit the beneficial therapeutic effects noted herein.

EXAMPLE II

Example I was repeated except that Stevia extract powder (available from Shaanxi Company) was substituted for the Lou Han extract powder at the same concentration. The same results were achieved.

EXAMPLE III

Example I was repeated except that Chinese Blackberry extract powder (available from Shaanxi Company) was substituted for the Lou Han extract powder at the same concentrations. The same results were achieved.

EXAMPLE IV

A cranberry based dietary supplement was prepared using the following ingredients:

| Component | % by Weight |
| --- | --- |
| Whole cranberry power | 1.0 |
| Lou Han extract powder | 1.5 |
| Fructose | 2.5 |
| Chinese licorice extract | 0.1 |
| Natural cranberry flavor | 2.5 |
| Glycerin | 33.0 |
| Water | 50.4 |

The foregoing ingredients were blended to form a pleasant tasting dietary supplement which is believed to exhibit the beneficial therapeutic effects noted herein.

EXAMPLE V

A cranberry based dental gel was prepared using the following ingredients:

| Component | % by Weight |
| --- | --- |
| Whole cranberry power | 5.0 |
| Lou Han extract powder | 1.5 |
| Chinese licorice extract | 0.1 |
| Gel base | 93.4 |

The foregoing ingredients were blended to form a beneficial dental gel.

What is claimed is:

1. A composition useful as a dietary supplement or an oral hygiene product, which composition comprises:
   (a) a source of cranberry selected from the group consisting of cranberry juice, cranberry juice concentrate, cranberry juice powder, cranberry whole fruit powder and combinations of the foregoing; and
   (b) at least one sweetener selected from the group consisting of (i) extracts of the fruits of Lou Han Kuo, (ii) extracts of the leaves of Stevia, and (iii) extracts of the leaves of Chinese Blackberry; and
   (c) extract of Chinese Licorice root; wherein each of the foregoing extracts has been extracted from its source using water, alcohol, or a water-alcohol mixture as the extractant.

2. A composition according to claim 1 wherein the composition also comprises at least one material selected from the group consisting of vitamins, fructose, glycerin, thickeners, gelling agents, xylitol.

3. A composition according to claim 1 wherein the composition is substantially free of sucrose.

4. A composition according to claim 1 wherein the concentration of the source of cranberry, on a dry basis, is from about 5% to 15% by weight.

5. A composition according to claim 1 wherein the concentration of the additive(s), on a dry basis, is from about 0.05% to 5.0% by weight.

6. A composition according to claim 1 wherein the concentration of extract of Chinese licorice root is from about 0.001% to 1.0%.

7. A composition according to claim 2 wherein the composition is substantially free of sucrose.

8. A composition according to claim 2 wherein the concentration of the source of cranberry, on a dry basis, is from about 5% to 15% by weight.

9. A composition according to claim 2 wherein the concentration of the additive(s), on a dry basis, is from about 0.05% to 5.0% by weight.

* * * * *